US00RE38408E

(19) United States
(12) Reissued Patent
Cao

(10) Patent Number: US RE38,408 E
(45) Date of Reissued Patent: Jan. 27, 2004

(54) METHODS OF PREPARING AND PURIFYING 9-NITRO-20-CAMPTOTHECIN

(75) Inventor: Zhisong Cao, Friendship, TX (US)

(73) Assignee: The Stehlin Foundation for Cancer Research, Houston, TX (US)

(21) Appl. No.: 09/591,605

(22) Filed: Jun. 9, 2000

Related U.S. Patent Documents

Reissue of:
(64) Patent No.: 5,922,877
Issued: Jul. 13, 1999
Appl. No.: 08/906,434
Filed: Aug. 5, 1997

(51) Int. Cl.[7] ..... C07D 491/147
(52) U.S. Cl. ..... 546/48
(58) Field of Search ..... 546/48; 514/283

(56) References Cited

U.S. PATENT DOCUMENTS

| | | | | |
|---|---|---|---|---|
| 4,981,968 | A | 1/1991 | Wall | 546/48 |
| 5,559,235 | A | 9/1996 | Luzzio et al. | 544/361 |
| 5,614,628 | A | 3/1997 | Cabri et al. | 546/48 |
| 5,731,316 | A | 3/1998 | Cao | 546/48 |

FOREIGN PATENT DOCUMENTS

| | | |
|---|---|---|
| HU | P9904210 A | 6/1998 |
| WO | WO 94/19353 | 9/1994 |
| WO | WO 95/09169 | 4/1995 |

OTHER PUBLICATIONS

Yakugaku Zasshi (1967), 87 (10), p1290–1292.

Cotton et al., "Advanced Inorganic Chemistry" Inter Science, New York, 1962 pp. 264–265.

Sawada et al. Chem. Pharm. Bull. vol. 39 (No. 2), pp. 3183–3188 (1991).

J.V. Crivello, "Nitrations and Oxidations with Inorganic Nitrate Salts in Trifluoroacetic Anhydride" *J. Org. Chem.,* vol. 46, No. 15, 1981.

*Primary Examiner*—Bruck Kifle
(74) *Attorney, Agent, or Firm*—Kilyk & Bowersox, P.L.L.C.

(57) ABSTRACT

A method is disclosed for the preparation of 9-nitrocamptothecin which involves reacting 20-camptothecin with at least one inorganic nitrate salt and at least one acid effective in catalyzing the formation of a nitronium ion, where the reaction occurs at a temperature and for a time sufficient to form the 9-nitrocamptothecin. Also, methods of further purifying the 9-nitrocamptothecin by column chromatography or by reprecipitation is also disclosed.

42 Claims, No Drawings

METHODS OF PREPARING AND PURIFYING 9-NITRO-20-CAMPTOTHECIN

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to method of preparing and purifying 9-nitro-20-camptothecin (9NC).

2. Description of Related Art 9-nitro-20(S)-camptothecin has shown great promise in treating certain types of cancer. The water-insoluble 9-nitro-20(S)-camptothecin has been studied both in vitro and in vivo and 9-nitro-20(S)-camptothecin is in clinical trials for certain types of cancer.

Japanese Kokai Patent Application No. 59-51288 provides one method of making 9-nitro-camptothecin by treating camptothecin with a slight excess of concentrated nitric acid in concentrated sulfuric acid. However, when following this procedure, a yield of about 3% to about 7% of the 9NC product which is capable for medicinal use is obtained. Further, this procedure results in unwanted byproducts such as the inactive isomer, 12-nitrocamptothecin (12NC), in a ratio of about 1 to 3 of 9NC to 12NC. The following scheme shows the reaction from the use of nitric acid and sulfuric acid.

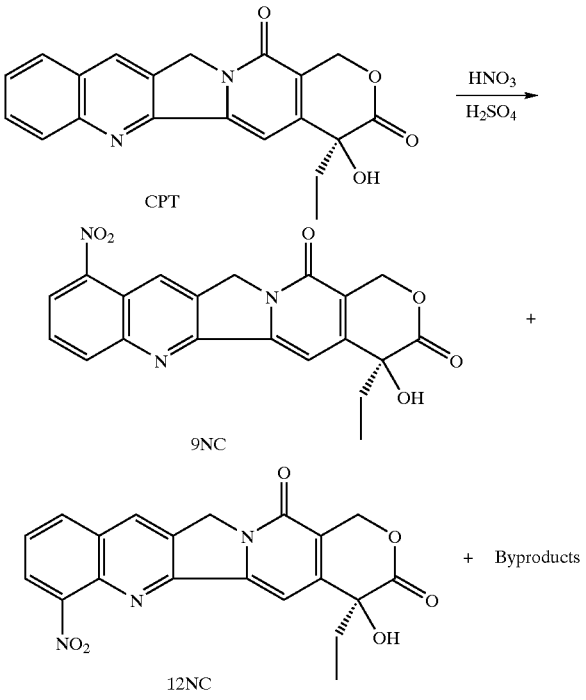

The unwanted 12NC, unfortunately, is the major product and accounts for about 60% of the yield. Because of the low yield of the 9NC and the numerous byproducts, the process of separating and purifying the 9NC is time consuming and costly and leads to a further decrease in the yield of 9NC. Accordingly, there is a need for a process that leads to a higher yield of 9NC and preferably without the numerous byproducts that have accompanied previous methods of making 9NC.

SUMMARY OF THE INVENTION

A feature of the present invention is to provide a method for the preparation of 9-nitrocamptothecin which preferably provides an increase in the yield of 9-nitrocamptothecin.

An additional feature of the present invention is to provide an improved purification procedure for purifying 9-nitrocamptothecin.

Additional features and advantages of the present invention will be set forth in part in the description which follows, and in part will be apparent from the description, or may be learned by practice of the present invention. The objectives and other advantages of the present invention will be realized and attained by means of the elements and combinations particularly pointed out in the written description and appended claims.

To achieve these and other advantages and in accordance with the purpose of the present invention, as embodied and broadly described herein, the present invention relates to a method for the preparation of 9-nitrocamptothecin. The method includes the steps of reacting 20-camptothecin with at least one inorganic nitrate salt and an acid which is effective in catalyzing the formation of a nitronium ion. The reaction occurs at a temperature and for a time sufficient to form the 9-nitrocamptothecin.

The present invention also relates to a method of purifying the 9-nitrocamptothecin by column chromatography which preferably uses an eluant comprising tetrahydrofuran and methylene chloride.

It is to be understood that both the foregoing general description and the following detailed description are exemplary and explanatory only and are intended to provide further explanation of the present invention, as claimed.

DETAILED DESCRIPTION OF THE PRESENT INVENTION

In general, the method for making 9-nitrocamptothecin involves reacting 20-camptothecin with at least one inorganic nitrate salt and an acid effective in catalyzing the formation of a nitronium ion from the nitrate salt. The reaction occurs at a temperature and for a time sufficient to form the 9-nitrocamptothecin.

With respect to the starting materials, the camptothecin can be any 20-camptothecin. Preferably, the 20-camptothecin is a racemic 20-camptothecin (i.e., 20(R, S)-camptothecin) or 20(S)-camptothecin. More preferably, the 20-camptothecin is 20(S)-camptothecin. The camptothecin is commercially available from such sources as Jingtao Science and Technology Development Co., Beijing, China. While any purity of camptothecin can be used, preferably, the 20-camptothecin has a purity of from about 85% to about 99%, more preferably at least about 92%. The amount of 20-camptothecin reacted with at least inorganic nitrate salt and an acid effective in catalyzing the formation of a nitronium ion can be any amount, as long sufficient amounts of the remaining ingredients are present.

The inorganic nitrate salt can be any salt which is capable of forming a nitronium ion which ultimately results in the nitro substituent attached at the 9-position of the camptothecin. Examples of inorganic salts include, but are not limited to, $KNO_3$; $NH_4NO_3$; $LiNO_3$; $AgNO_3$; $TiNO_3$; $BiONO_3$; $Cu(NO_3)_2$ 2.5 $H_2O$; $Hg(NO_3)_2$ $H_2O$; $Ca(NO_3)_2$ 4.$H_2O$; $Ba(NO_3)_2$; $Zn(NO_3)_2$ 6.$H_2O$; $Mg(NO_3)_2$ 6.$H_2O$; $Co(NO_3)_2$ 6.$H_2O$; $Sr(NO_3)_2$; $Pb(NO_3)_2$; $Al(NO_3)_3$ 9.$H_2O$; $Fe(NO_3)_3$ 9.$H_2O$; $Cr(NO_3)_3$ 9.$H_2O$; and $La(NO_3)_3$ 6.$H_2O$.

In the method of the present invention, at least one inorganic nitrate salt is used in the reaction. More than one inorganic nitrate salt can be used, for instance, two or three or more different inorganic nitrate salts can be used in the same reaction. Certain combinations of inorganic nitrate salts have lead to improved results with respect to the percent yield of 9-nitrocamptothecin and a more favorable ratio of the present of 9-nitrocamptothecin yield to the percent of 9-nitrocamptothecin yield as well as a higher total percent of nitration and/or a lower percent of byproducts resulting from the reaction.

Specific examples of combinations of inorganic nitrate salts include, but are not limited to, $KNO_3$ and $Cu(NO_3)_2$ $2.5.H_2O$; $KNO_3$ and $TiNO_3$; $KNO_3$ and $Hg(NO_3)_2$ $H_2O$; $KNO_3$ and $Ca(NO_3)_2$ $4.H_2O$; $KNO_3$ and $Ba(NO_3)_2$; $KNO_3$ and $Zn(NO_3)_2$ $6.H_2O$; $KNO_3$ and $Sr(NO_3)_2$; $KNO_3$ and $Pb(NO_3)_2$; $KNO_3$ and $Al(NO_3)_3 9.H_2O$; $KNO_3$ and $Fe(NO_3)_3$ $9.H_2O$; $LiNO_3$ and $Hg(NO_3)_2.H_2O$; $LiNO_3$ and $Cu(NO_3)_2$ $2.5.H_2O$; $LiNO_3$ and $Co(NO_3)_2$ $6.H_2O$; $AgNO_3$ and $Cr(NO_3)_3$ $9.H_2O$; $Cu(NO_3)_2$ $2.5.H_2O$ and $Fe(NO_3)_3$ $9.H_2O$; $Hg(NO_3)_2.H_2O$ and $Fe(NO_3)_3$ $9.H_2O$; $NH_4NO_3$ and $Cu(NO_3)_2$ $2.5.H_2O$; $KNO_3$, $TiNO_3$, and $Cu(NO_3)_2$ $2.5$ $H_2O$; $KNO_3$, $TiNO_3$, and $Zn(NO_3)_2$ $6.H_2O$; $KNO_3$, $TiNO_3$, and $Pb(NO_3)_2$; $KNO_3$, $Cu(NO_3)_2$ $2.5.H_2O$, and $Fe(NO_3)_3$ $9.H_2O$; $KNO_3$, $LiNO_3$, $Cu(NO_3)_2$ $2.5.H_2O$, $Hg(NO_3)H_2O$, and $Fe(NO_3)_2$ $H_2O$; $Zn(NO_3)_2$ $6.H_2O$; $KNO_3$, $LiNO_3$, $AgNO_3$, $Cu(NO_3)_2$ $2.5.H_2O$, $Hg(NO_3)_2$ $H_2O$, and $Fe(NO_3)_3$ $9.H_2O$; $KNO_3$, $LiNO_3$, $Zn(NO_3)_2$ $6.H_2O$. $Cu(NO_3)_2$ $2.5$ $H_2O$, $Hg(NO_3)_2$ $H_2O$, and $Fe(NO_3)_3$ $9.H_2O$; and $KNO_3$, $Zn(NO_3)_2$ $6.H_2O$, $Cu(NO_3)_2$ $2.5.H_2O$, $Hg(NO_3)_2$ $H_2O$, and $Fe(NO_3)_3$ $9.H_2O$.

The amount of inorganic nitrate salt present in the reaction (as compared with the amount of camptothecin used in the reaction) is in excess of the amount of camptothecin used and more preferably is from about 2 times to about 3 times by mole more than the 2-camptothecin present. The inorganic nitrate salts are commercially available from such sources as Aldrich Chemical Co., Milwaukee, Wis.

With respect to the acid used in the method of the present application, the acid is effective in catalyzing the formation of a nitronium ion. Examples of acids include, but are not limited to, concentrated sulfuric acid, trifluoroacetic acid, or trifluoroacetic acid anhydride. By the use of the term "concentrated," the sulfuric acid should have a concentration of at least about 95% and more preferably from about 96% to about 98%. The amount of acid used in the reaction should be in the range of 50 ml to 120 ml/gram of 20-CPT, more preferably, 100 ml/gram of 20-CPT.

In conducting the method of the present application, generally, the starting materials can be added to a reaction vessel in any sort of order and mixed together until the formation of the 9-nitrocamptothecin. While the order that the starting materials are added to the reaction vessel is not critical, it is preferred that the acid is first added to the reaction vessel which is equipped with a magnetic stirrer, for instance, and then the camptothecin and inorganic nitrate salt are added. Preferably, the mixture is stirred at room temperature for at least about 72 hours, more preferably from about 72 hours to about 96 hours. Once the mixture has been stirred for a sufficient time, the mixture can be poured in portioned amounts onto ice-water while stirring to avoid over-heating. The suspension formed can then be extracted with a solvent such as methylene chloride and the extracts can be dried over, for instance, sodium sulfate for several hours.

As shown in Table 1, the reaction scheme is shown where the nitration of camptothecin 1 with inorganic nitrate salt gave 9-nitrocamptothecin 4, 12-nitrocamptothecin 5, and other by-products. A preferred nitration reaction is where a favorable ratio of 9-nitrocamptothecin to 12-nitrocaptothecin is achieved as well as a higher total nitration yield and a low yield by percent of by-products. Table 2 provides a summary of the nitration reaction of camptothecin with common inorganic salts in concentrated sulfuric acid. From the results, it can be seen that $TiNO_3$ and $KNO_3$ were the preferred inorganic nitrate salts based on the yield of 9-nitrocamptothecin and/or the ratio of 9-nitrocamptothecin to 12-nitrocamptothecin obtained. Table 3 provides data showing several combinations of two different inorganic nitrate salts used in the reaction to form 9-nitrocamptothecin. From Table 3, it can be seen that combinations like $KNO_3/TiO_3$; $KNO_3/Zn(NO_3)_2$; and $KNO_3/Sr(NO_3)_2$ were preferred from the results achieved. For instance, the combination of $KNO_3/TiO_3$ provided an improved ratio of 9-nitrocamptothecin to 12-nitrocamptothecin of 1:1.4, as well as a higher yield of 9-nitrocamptothecin which was 29% when compared to the results obtained from the reaction using potassium nitrate or thallium nitrate individually as the nitrating agent. Also, the combination of $KNO_3$ and $Hg(NO_3)_2$ also showed an improved ratio of 9-nitrocamptothecin to 12-nitrocamptothecin of 1 to 1.2. Table 4 summarizes the use of three of more inorganic nitrate salts as the nitrating reagents and shows that such combinations are possible.

Table 5 summarizes the results of the nitration of camptothecin with a combination of potassium nitrate and thallium nitrate with different ratios in concentrated sulfuric acid. From Table 5, it can be seen that a higher percent yield of 9-nitrocamptothecin as well as an improved ratio of 9-nitrocamptothecin to 12-nitrocamptothecin can be obtained when the preferred combination of the inorganic nitrate salts is in the ratio range of 1.4/1.0 to 1.0/1.5 of $KNO_3$ to $TiNO_3$. More preferably 1.3/1.0 to 1.0/1.0 of $KNO_3$ to $TiNO_3$ is used. With such a ratio range, a consistent yield of 20±1 percent of pure 9-nitrocamptothecin can be obtained where conventional methods would obtain at most 5±2 percent.

The present invention will be further clarified by the following examples, which are intended to be purely exemplary of the invention.

EXAMPLES

In the following examples, all glassware was baked at 70±10° C. for a minimum of 2 hours before being used. Melting points were obtained with a MEL-TEMP melting point apparatus and were uncorrected. The $^1H$ NMR spectrum of approximately 10% (w/v) solution in $CDCl_3$ were obtained at 270.05 $MN_z$ with a JEOL GX-270 WB NMR spectrometer. Chemical shifts are reported in parts per millions (δ scale), employing tetramethylsilane as an internal standard. In reporting the NMR data, we have used the following abbreviations: coupling constants in Hertz (J), singlets (s), doublet (d), triplet (t), broad single (bs), multiplet (m), and the like. Mass Spectra were recorded using a VG ZAB-SEQ mass spectrometer (VG Analytical Co., England) with a resolution of 10000. Routinely used solvents such as chloroform and methylene chloride were dried and freshly distilled. Silica gel (230–400 mesh, Aldrich) for column chromatography was used for all product separations. Eastman chromagram (Silica gel with fluorescent indicator on polyethylene) sheets were employed in thin-layer chromatography (TLC) operations. The number system used in reporting NMR data is shown in structure 1 in Table 1.

20(S)-camptothecin was purchased from Jingtao Science and Technology Development Co., Beijing, The People's Republic of China and used as purchased. All other inorganic nitrate salts were purchased from Aldrich Chemical Co. (Milwaukee, Wis.) and used as purchased as well.

The concentrated sulfuric acid was 96% concentrated and was obtained from Fisher and was used as received.

Example 1

Reaction of Camptothecin With $KNO_3$ in Acetic Acid

To 30 ml acetic acid in a 100 ml round-bottomed flask equipped with a magnetic stirrer were added 0.50 g (0.0014 mol) 20(S)-camptothecin and 0.50 g $KNO_3$ (0.0050 mol). The mixture was stirred at room temperature for 24 hours and poured onto 500 ml ice-water in several portions while stirring. The suspension was extracted three times with 200 ml methylene chloride each time (200 ml×3). The combined extracts were dried over 200 g anhydrous sodium sulfate for 6 hours. After removal of methylene chloride by a rotary evaporator, the residue was refluxed in petroleum ether for 4 hours. After filtration and drying in air for 4 hours the product obtained was a gray white powder. HPLC analysis showed no nitration indicative of camptothecin with $KNO_3$ in acetic acid. The starting camptothecin was recovered 100% (Table 1).

Example 2

Reaction of Camptothecin With $KNO_3$ in Acetic Anhydride

Camptothecin was nitrated and worked-up in the same manner as the reaction in Example 1. The HPLC analysis of the reaction product showed 100% recovery of the starting camptothecin (Table 1).

Example 3

Reaction of Camptothecin With $KNO_3$ in Trifluoroacetic Anhydride

Camptothecin was nitrated and work-up in the same manner as in Example 1. The HPLC analysis data for the reaction mixture is shown in Table 1.

Example 4

Nitration of Camptothecin With $KNO_3$ in Concentrated Sulfuric Acid

Camptothecin (0.50 g, 0.0014 mol) and potassium nitrate (0.50 g, 0.0050 mol) were added to 30 ml concentrated sulfuric acid in a 100 ml round-bottomed flask equipped with a magnetic stirrer all at once. The mixture was stirred at room temperature for a day and then poured onto 500 ml ice-water slowly while stirring. The yellow suspension was extracted three times with 200 ml methylene chloride each time (200 ml×3). The combined extracts were dried over anhydrous sodium sulfate for a day. The methylene chloride was removed by a rotary evaporator and the residue was refluxed in petroleum ether for 4 hours. After cooling to room temperature, the mixture was filtrated and the yellow powder obtained was dried in air for a day. The HPLC analysis data for the reaction mixture (yellow powder) is shown in Table 1.

Example 5

Nitration of Camptothecin With Various Nitrates in Sulfuric Acid

Camptothecin (0.50 g, 0.0014 mol) and ammonium nitrate (0.56 g, 0.0070 mol) were added to 20 ml concentrated sulfuric acid in a 100 ml round-bottomed flask equipped with a magnetic stirrer. The mixture was stirred at room temperature for 72 hours after which it was poured onto 500 ml ice-water while stirring, extracted three times with 200 ml methylene chloride each time (200 ml×3). The combined extracts were washed two times with 100 ml water each time (100 ml×2). The two washes were combined and extracted two times with 100 ml methylene chloride each time (100 ml×2). All extracts (~600 ml+~200 ml) were combined, dried ($Na_2SO_4$, 20 g) for 4 hours and then evaporated to give crude reaction products as a yellow powder which contained 9NC (19%), 12NC (41%), unreacted camptothecin (25%), and other byproducts (15%)

The results of HPLC analyses for all these reactions are shown in Table 2.

Example 6

Nitration of Camptothecin With a Combination of Two Different Nitrates in Sulfuric Acid Camptothecin (4.0 g, 0.0115 mol) was added to 100 ml concentrated sulfuric acid in a 250 ml three-necked flask. The suspension was stirred with a mechanic stirrer until the most of camptothecin went into solutions (~15 to 30 min). To this solution, $KNO_3$ (2.32 g, 0.0230 mol) and $Cu(NO_3)_2.2.5H_2O$ (2.67 g, 0.0115 mol) were added all at once. The mixture was stirred at room temperature for 72 hours and poured onto 1500 ml ice-water while stirring. The yellow suspension in water was extracted four times with 500 ml methylene chloride each time (500 ml×4). The combined extracts was dried over anhydrous sodium sulfate for 8 hours. The sodium sulfate was removed by filtration. After removal of methylene chloride by a rotary evaporator, the crude reaction products were obtained as a yellow powder, containing 9NC (24%), 12NC (50%), unreacted camptothecin (6%), and other byproducts (20%). The results of HPLC analyses for all these nitration reactions are shown in Table 3.

Example 7

Nitration of Camptothecin With a Combination of Three or More Inorganic Nitrates in Sulfuric Acid Camptothecin (4.0 g, 0.0115 mol) was suspended in 100 ml concentrated sulfuric acid in a 250 ml round-bottomed flask equipped with a mechanic stirrer. After stirring for ~30 min (until camptothecin was almost dissolved), a combination of $KNO_3$ (1.16 g, 0.0115 mol), $TiNO_3$ (3.10 g, 0.0116 mol), and $Cu(NO_3)_2.2.5H_2O$ (2.67 g, 0.0115 mol) was added all at once. The mixture was stirred at room temperature for 72 hours and then poured onto 1500 ml ice-water while stirring. The yellow suspension was extracted four times with 500 ml methylene chloride each time (500 ml×4). The combined extracts were dried over anhydrous sodium sulfate, filtered, and evaporated. The crude reaction products were obtained as a yellow powder, containing 9NC (25%), 12NC (44%), unreacted camptothecin (10%), and other byproducts (21%). The results of HPLC analyses for all these nitration reactions are shown in Table 4.

Example 8

Nitration of Camptothecin With Different Ratios of a Combination of $KNO_3$ and $TiNO_3$ in Sulfuric Acid Camptothecin (6.0 g, 0.0172 mol) was added to 100 ml concentrated sulfuric acid in a 250 ml three-necked flask equipped with a mechanic stirrer. After stirring at room temperature for ~30 min, a combination of $KNO_3$ (1.74 g, 0.0172 mol) and $TiNO_3$ (4.58 g, 0.0172 mol) was added all at once. The mixture was stirred at room temperature for 72 hours and then poured on to 1500 ml ice-water while stirring. The yellow suspension was extracted four times with 500 ml methylene chloride each time (500 ml×4). The combined extracts were dried over anhydrous $Na_2SO_4$ for 8 hours. After removal of methylene chloride by a rotary evaporator, the crude reaction products were obtained as a yellow powder, containing 9NC (26%), 12NC (49%), unreacted camptothecin (11 %), and other byproducts (14%). The results of HPLC analyses for all these reactions are shown in Table 5.

Example 9

Nitration of Camptothecin With a Combination of $KNO_3$ and $TiNO_3$ (Ratio: 1.0/1.3) in Various Volumes of Sulfuric Acid The general procedure of Example 8 was followed, except $KNO_3$ and $TiNO_3$ were used with various volumes of sulfuric acid as indicated in Table 6. The results are also shown in Table 6.

Example 10

A Procedure For the Preparation of 9-Nitrocamptothecin

Camptothecin (4.0 g, 0.0115 mol) was added to 300 ml concentrated sulfuric acid in a 1000 ml three-necked flask. After stirring for ~15 min, $KNO_3$ (2.0 g, 0.0198 mol) and $TiNO_3$ (5.0 g, 0.0188 mol) were added all at once. The mixture was stirred at room temperature for 72 hours and then poured onto 3500 ml ice-water while stirring. The yellow suspension was extracted three times with a total of 3300 ml methylene chloride (1500 ml×1, and 900 ml×2). The combined extracts were dried over anhydrous sodium sulfate for 8 hours. After filtration, the solvents were removed by a rotary evaporator. The residue was chromatographically separated. The crude 9-nitrocamptothecin was allowed to reflux in absolute ethanol for 2–4 hours. The pure product (9NC), obtained by reprecipitation from ethanol, was a bright yellow powder, (mp 268° C., yield 20%). $^1H$ NMR: 1.05 (3H, t, J=7.40 Hz, C19-methyl protons), 1.92 (2H, m, C18-methylene protons), 3.82 (1H, s, C20-OH), 5.40 (2H, s, C5-methylene protons), 5.55 (2H, dd, J=14.21 Hz, 14.21 Hz, C17-methylene protons), 7.70 (1H, s, C14-H), 7.92(1H, t, J=8.40 Hz, C11-H), 8.48 (1H, d, J=8.35 Hz, C10-H), 8.55 (1H, d, J=8.35 Hz, C12-H), 9.36 (1H, s, C7-H); mass m/e(relative intensity): 393 ($M^+$, 100%), 364 ($M-CH_2H_5$, 35%), 349 (48%), 334 (25%), 320 (25%), 293 (35%), 274 (8%), 262 (8%), 246 (15%), 234 (6%), 218 (20%), 205 (8%), 190 (9%), 177 (5%), 164 (3%), 151(3%), 137(5%), 123(4%), 109 (5%), 95 (5%), 75 (3%), 60 (23%); precise mass: 393.096 (found), 393.096 (required for $C_{20}H_{15}N_3O_6$).

Example 11

HPLC Purity Analysis of 9-Nitrocamptothecin

Instrumentation: The HPLC system consisted of a Beckman 421 controller with two 110A pumps and a 2 ml injection loop. The UV detector was a SPD-110AV model (Shimadzu, Kyoto, Japan). The HPLC detector was set to monitor the UV absorbance at 220 nm. The integrating software used for the analyses was EZChrome (Shimadzu, Japan) and FLO-ONe/beta (Radiomatic Instruments, Meridian, Conn.). A C-8 Microsorb was from Rainin Instruments (Woburn, Mass.). HPLC analysis: Reverse phase HPLC analysis of the samples was carried out by using an acetonitrile-acetic acid-water mobile phase system. Analyses were carried out at room temperature with a flow rate 1 ml/min. The solution with a concentration of approximately 0.1 mg/ml of 9NC in acetonitrile was prepared by dissolving it in the solvent. A 300 $\mu$l portion of this solution was taken and added to 700 $\mu$l solution of 0.1% acetic acid in water. After shaking for ~10 s, 100 $\mu$l of this solution was injected through a 2 ml loop onto a column and chromatographed with 70% water with 0.1% acetic acid and 30% acetonitrile as the mobile phase for the period of first 5 min. and then the gradient of the mobile phase was programmatically increased to 100% acetonitrile over a period of 4 min. A complete HPLC spectrum was obtained in 15 min. The purity of 9NC was determined by measuring the UV peak areas at 254 nm and calculating the percentage associated with the 9NC peak. The purity of 9NC was at least 96%. The retention time of 9-nitrocamptothecin under these conditions is approximately 6.5 minutes.

TABLE 1

Nitration of Camptothecin with $KNO_3$ in Different Solvents[a]

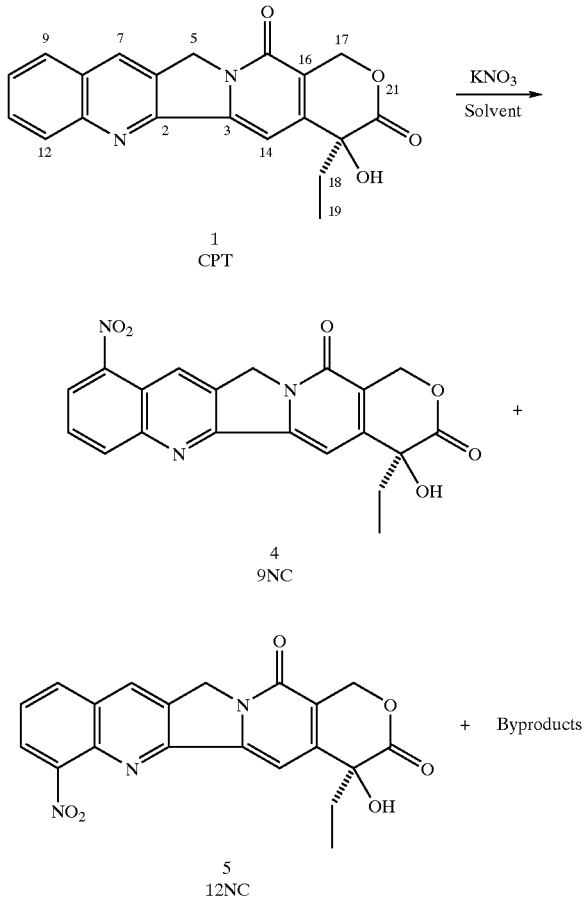

| Solvent | % 9NC | % 12NC | % CPT[c] | % By-products | 9NC[d]/12NC[d] | % Total nitration |
|---|---|---|---|---|---|---|
| Acetic acid | 0 | 0 | 100 | 0 | 0/0 | 0 |
| Acetic anhydride | 0 | 0 | 100 | 0 | 0/0 | 0 |
| TFAA[b] | 4 | 8 | 23 | 65 | 1/2 | 12 |
| Sulfuric acid | 21 | 47 | 26 | 6 | 1/2.2 | 68 |

[a]Camptothecin: 0.5 g, potassium nitrate: 0.5 g, solvent: 30 ml, reaction time: 24 hr, reacton temperature: rt.

[b]TFAA represents trifluoroacetic anhydride.

[c]% CPT represents the % recovery of camptothecin and CPT represents camptothecin.

[d]9NC represents 9-nitrocamptothecin and 12NC represents 12-nitrocamptothecin.

TABLE 2

Nitration of Camptothecin with Various Nitrates in Sulfuric Acid[a]

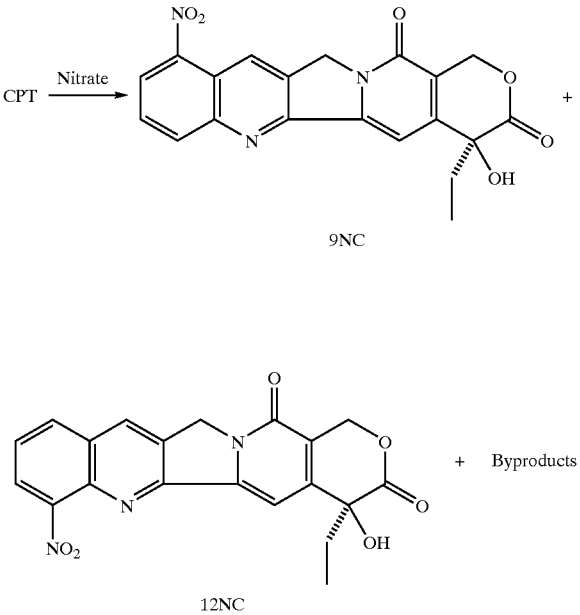

| Nitrate | % 9NC | % 12NC | % CPT | % By-products | 9NC/12NC | % Total nitration |
|---|---|---|---|---|---|---|
| $NH_4NO_3$ | 19 | 41 | 25 | 15 | 1/2.2 | 60 |
| $KNO_3$ | 23 | 52 | 19 | 6 | 1/2.3 | 75 |
| $LiNO_3$ | 22 | 38 | 0 | 40 | 1/1.7 | 60 |
| $AgNO_3$ | 19 | 43 | 18 | 20 | 1/2.3 | 62 |
| $TiNO_3$ | 24 | 49 | 15 | 12 | 1/2.0 | 73 |
| $BiONO_3$ | 11 | 17 | 48 | 24 | 1/1.5 | 28 |
| $Cu(NO_3)_2 2.5H_2O$ | 22 | 53 | 1 | 24 | 1/2.4 | 75 |
| $Hg(NO_3)_2H_2O$ | 22 | 43 | 1 | 35 | 1/2.0 | 65 |
| $Ca(NO_3)_2 4H_2O$ | 20 | 49 | 1 | 30 | 1/2.5 | 69 |
| $Ba(NO_3)_2$ | 17 | 54 | 3 | 20 | 1/3.2 | 71 |
| $Zn(NO_3)_2 6H_2O$ | 21 | 44 | 19 | 16 | 1/2.1 | 65 |
| $Mg(NO_3)_2 6H_2O$ | 23 | 45 | 9 | 23 | 1/2.0 | 68 |
| $Co(NO_3)_2 6H_2O$ | 21 | 41 | 0 | 38 | 1/2.0 | 62 |
| $Sr(NO_3)_2$ | 22 | 36 | 1 | 41 | 1/1.6 | 58 |
| $Pb(NO_3)_2$ | 18 | 50 | 13 | 19 | 1/2.8 | 68 |
| $Al(NO_3)_3 9H_2O$ | 17 | 46 | 1 | 36 | 1/2.7 | 63 |
| $Fe(NO_3)_3 9H_2O$ | 23 | 51 | 0 | 26 | 1/2.2 | 74 |
| $Cr(NO_3)_3 9H_2O$ | 13 | 28 | 46 | 13 | 1/2.2 | 41 |
| $La(NO_3)_2 6H_2O$ | 11 | 34 | 2 | 54 | 1/3.1 | 45 |

*For each reaction: Camptothecin: 0.5 g (0.0014 mol), $H_2SO_4$: 20 ml, Nitrate: 0.0070 mol, 72 hr, and room temp.

TABLE 3

Nitration of Camptothecin with A Combination of Two Different Nitrates in Sulfuric Acid[a]

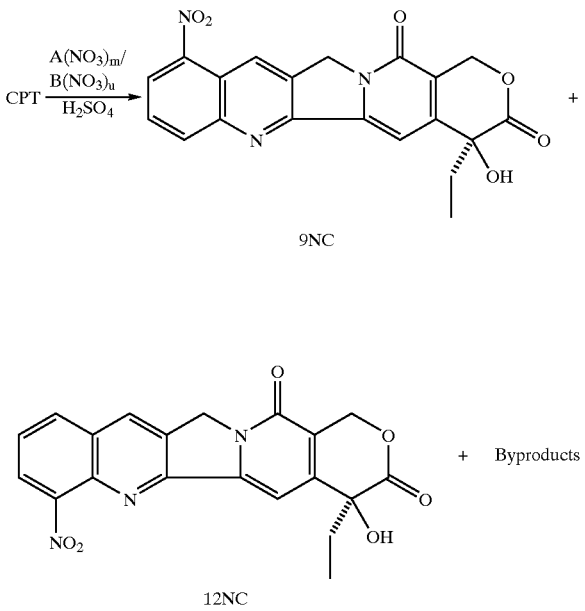

| $A(NO_3)_m$/ $B(NO_3)_n$[b] | % 9NC | % 12NC | % CPT | % Byproducts | 9NC/12NC | % Total nitration |
|---|---|---|---|---|---|---|
| K/Cu[c] | 24 | 50 | 6 | 20 | 1/2.1 | 74 |
| K/Ti | 29 | 41 | 8 | 22 | 1/1.4 | 70 |
| K/Hg | 21 | 25 | 12 | 42 | 1/1.2 | 46 |
| K/Ca | 18 | 42 | 3 | 37 | 1/2.3 | 60 |
| K/Ba | 20 | 39 | 0 | 41 | 1/2.0 | 59 |
| K/Zn | 26 | 50 | 10 | 14 | 1/1.9 | 56 |
| K/Sr | 29 | 45 | 3 | 23 | 1/1.6 | 74 |
| K/Pb | 24 | 49 | 12 | 15 | 1/2.0 | 73 |
| K/Al | 25 | 50 | 2 | 23 | 1/2.0 | 75 |
| K/Fe | 18 | 41 | 0 | 41 | 1/2.3 | 59 |
| Li/Hg | 17 | 38 | 17 | 26 | 1/2.2 | 55 |
| Li/Cu | 22 | 47 | 10 | 21 | 1/2.1 | 69 |
| Li/Co | 11 | 30 | 2 | 57 | 1/2.7 | 41 |
| Ag/Cr | 18 | 37 | 1 | 44 | 1/2.1 | 55 |
| Cu/Fe | 17 | 33 | 1 | 49 | 1/1.9 | 50 |
| Hg/Fe | 23 | 45 | 2 | 30 | 1/2.0 | 68 |
| $NH_4$/Cu | 17 | 49 | 2 | 32 | 1/2.9 | 66 |

[a]For each reaction: Camptothecin: 4.0 g (0.0115 mol), sulfuric acid: 100 ml, 72 hr, and room temperature.

[b]Molar ratio of $A(NO_3)_m$ to $B(NO_3)_n$: 2.0:1.0

[c]K/Cu represents the corresponding $KNO_3/Cu(NO_3)_2$ 2.5 $H_2O$, same applied to the other combinations.

TABLE 4

Nitration of Camptothecin with A Combination of Three or More Nitrates in Sulfuric Acid[a]

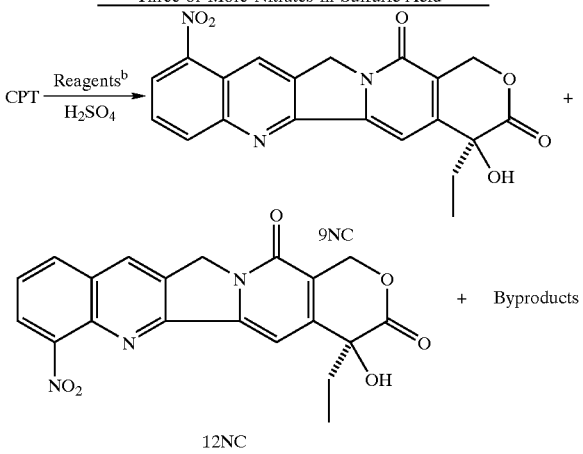

| Reagents | % 9NC | % 12NC | % CPT | % Byproducts | 9NC/12NC | % Total nitration |
|---|---|---|---|---|---|---|
| K/Ti/Cu[c] | 25 | 44 | 10 | 21 | 1.0/1.8 | 69 |
| K/Ti/Zn | 25 | 46 | 0 | 29 | 1.0/1.8 | 71 |
| K/Ti/Pb | 25 | 46 | 5 | 24 | 1.0/1.8 | 71 |
| K/Cu/Fe | 22 | 48 | 6 | 24 | 1.0/2.2 | 70 |
| K/Cu/Hg/Zn | 24 | 57 | 2 | 17 | 1.0/2.4 | 81 |
| K/Li/Cu/Hg/Fe | 21 | 44 | 12 | 23 | 1.0/2.1 | 65 |
| K/Li/Ag/Cu/Hg/Fe | 24 | 50 | 4 | 22 | 1.0/2.1 | 74 |
| K/Li/Zn/Cu/Hg/Fe | 23 | 44 | 7 | 30 | 1.0/1.9 | 67 |
| K/Zn/Cu/Hg/Fe | 26 | 50 | 4 | 20 | 1.0/1.9 | 76 |

[a]For each reaction: Camptothecin: 4.0 g (0.0115 mol), sulfuric acid: 100 ml, 72 hr, and room temperature.
[b]Molar ratio for all nitrates in a combination of the reagents is 1 to 1 to 1 . . .
[c]K/Ti/Cu represents the corresponding $KNO_3/TiNO_3/Cu(NO_3)_2\ 2.5H_2O$, same applied to other reagents.

TABLE 5

Nitration of Camptothecin with Different Ratios of A Combination of $KNO_3$ and $TiNO_3$ in Sulfuric Acid[a]

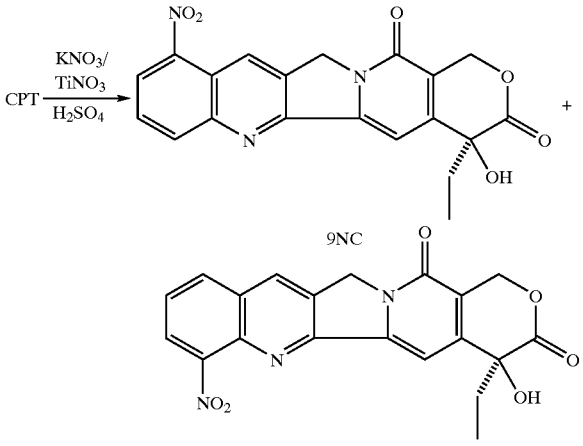

| $KNO_3$/ $TiNO_3$ | % 9NC | % 12NC | % CPT | % Byproduct | 9NC/12NC 9NC/12NC | % Total nitration |
|---|---|---|---|---|---|---|
| 3.3/1.0 | 26 | 47 | 5 | 22 | 1.0/1.8 | 73 |
| 2.0/1.0 | 29 | 41 | 8 | 22 | 1.0/1.4 | 70 |
| 1.4/1.0 | 27 | 46 | 10 | 17 | 1.0/1.7 | 73 |
| 1.3/1.0 | 28 | 49 | 6 | 17 | 1.0/1.8 | 77 |

TABLE 5-continued

Nitration of Camptothecin with Different Ratios of A Combination of $KNO_3$ and $TiNO_3$ in Sulfuric Acid[a]

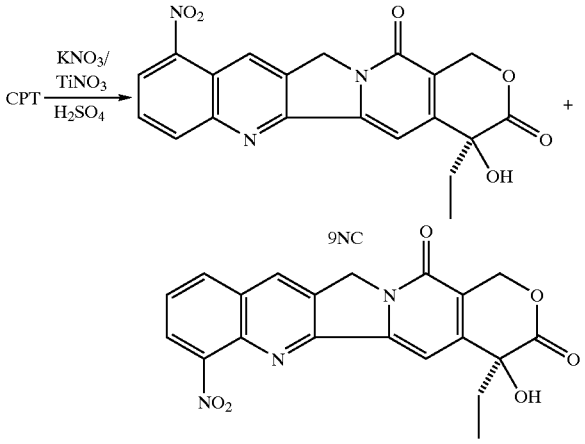

| $KNO_3$/ $TiNO_3$ | % 9NC | % 12NC | % CPT | % Byproduct | 9NC/12NC 9NC/12NC | % Total nitration |
|---|---|---|---|---|---|---|
| 1.2/1.0 | 27 | 50 | 8 | 15 | 1.0/1.9 | 77 |
| 1.0/1.0 | 26 | 49 | 11 | 14 | 1.0/1.9 | 75 |
| 1.0/1.3 | 27 | 49 | 11 | 13 | 1.0/1.8 | 76 |
| 1.1/1.5 | 26 | 47 | 12 | 15 | 1.0/1.8 | 73 |
| 1.0/2.1 | 25 | 38 | 9 | 28 | 1.0/1.5 | 63 |

[a]For each reaction: Camptothecin: 6.0 g (0.0172 mol), sulfuric acid: 100 ml, 72 hr, and room temperature.

TABLE 6

Effects of the volumes of concentrate sulfuric acid on the Nitration of of Camptothecin with a combination of $KNO_3$ and $TiNO_3$[a]

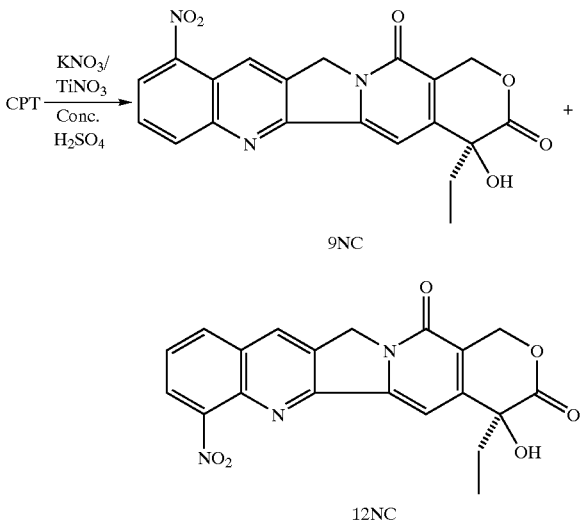

| $H_2SO_4$ (ml) | % 9NC | % 12NC | % CPT | % Byproducts | 9NC/12NC | % Total nitration |
|---|---|---|---|---|---|---|
| 100 | 29 | 41 | 08 | 22 | 1.0/1.4 | 70 |
| 200 | 25 | 49 | 15 | 11 | 1.0/2.0 | 74 |
| 300 | 28 | 53 | 09 | 10 | 1.0/1.9 | 81 |
| 400 | 29 | 45 | 10 | 16 | 1.0/1.6 | 74 |

[a]Camptothecin: 4.0 g, potassium nitrate: 2.0 g, thallium nitrate: 4.0 g, reaction time: 72 hr, reaction temperature: rt.

It is to be understood that both the foregoing general description and the following detailed description are exemplary and explanatory only and are intended to provide further explanation of the present invention, as claimed.

What is claimed is:

1. A method for the preparation of 9-nitrocamptothecin comprising:

reacting 20-camptothecin with at least one inorganic nitrate salt capable of forming a nitrobium ion and at least one acid effective in catalyzing the formation of a nitronium ion, at a temperature and for a time sufficient to form said 9-nitrocamptothecin.

2. The method of claim 1, wherein said 20-camptothecin is racemic 20-camptothecin or 20(S)-camptothecin.

3. The method of claim 2, wherein said 20-camptothecin is 20(S)-camptothecin, and said 9-nitrocamptothecin is 9-nitro-20(S)-camptothecin.

4. The method of claim 1, wherein said acid is concentrated sulfuric acid, trifluoroacetic acid, or trifluoroacetic acid anhydride.

5. The method of claim 4, wherein said acid is concentrated sulfuric acid.

6. The method of claim 1, wherein said inorganic nitrate salt is $KNO_3$; $NH_4NO_3$; $LiNO_3$; $AgNO_3$; $TiNO_3$; $BiONO_3$; $Cu(NO_3)_2 2.5.H_2O$; $Hg(NO_3)_2$ $4.H_2O$; $Ba(NO_3)_2$; $Zn(NO_3)_2$ $6.H_2O$; $Mg(NO_3)_2$ $6.H_2O$; $Co(NO_3)_2$ $6.H_2O$; $Sr(NO_3)_2$; $Pb(NO_3)_2$; $Al(NO_3)_3$ $9.H_2O$; $Fe(NO_3)_2$ $9.H_2O$; $Cr(NO_3)_3$ $9.H_2O$; $La(NO_3)_3$ $6.H_2O$; or mixtures thereof.

7. The method of claim 1, wherein said inorganic nitrate salt is a mixture of at least two inorganic nitrate salts.

8. The method of claim 7, wherein said inorganic nitrate salt comprises $KNO_3$ and at least one other inorganic nitrate salt.

9. The method of claim 7, wherein said inorganic nitrate salt comprises $KNO_3$ and $Cu(NO_3)_2$ $2.5.H_2O$.

10. The method of claim 7, wherein said inorganic nitrate salt comprises $KNO_3$ and $TiNO_3$.

11. The method of claim 7, wherein said inorganic nitrate salt comprises $KNO_3$ and $Hg(NO_3)_2$ $H_2O$.

12. The method of claim 7, wherein said inorganic nitrate salt comprises $KNO_3$ and $Ca(NO_3)_2$ $4.H_2O$.

13. The method of claim 7, wherein said inorganic nitrate salt comprises $KNO_3$ and $Ba(NO_3)_2$.

14. The method of claim 7, wherein said inorganic nitrate salt comprises $KNO_3$ and $Zn(NO_3)_2$ $6.H_2O$.

15. The method of claim 7, wherein said inorganic nitrate salt comprises $KNO_3$ and $Sr(NO_3)_2$.

16. The method of claim 7, wherein said inorganic nitrate salt comprises $KNO_3$ and $Pb(NO_3)_2$.

17. The method of claim 7, wherein said inorganic nitrate salt comprises $KNO_3$ and $Al(NO_3)_3$ $9.H_2O$.

18. The method of claim 7, wherein said inorganic nitrate salt comprises $KNO_3$ and $Fe(NO_3)_3$ $9.H_2O$.

19. The method of claim 7, wherein said inorganic nitrate salt comprises $LiNO_3$ and $Hg(NO_3)_2.H_2O$.

20. The method of claim 7, wherein said inorganic nitrate salt comprises $LiNO_3$ and $Cu(NO_3)_2$ $2.5.H_2O$.

21. The method of claim 7, wherein said inorganic nitrate salt comprises $LiNO_3$ and $Co(NO_3)_2$ $6.H_2O$.

22. The method of claim 7, wherein said inorganic nitrate salt comprises $AgNO_3$ and $Cr(NO_3)_3$ $9.H_2O$.

23. The method of claim 7, wherein said inorganic nitrate salt comprises $Cu(NO_3)_2$ $2.5.H_2O$ and $Fe(NO_3)_3$ $9.H_2O$.

24. The method of claim 7, wherein said inorganic nitrate salt comprises $Hg(NO_3)_2$ $.H_2O$; and $Fe(NO_3)_3$ $9.H_2O$.

25. The method of claim 7, wherein said inorganic nitrate salt comprises $NH_4NO_3$ and $Cu(NO_3)_2$ $2.5.H_2O$.

26. The method of claim 7, wherein said inorganic nitrate salt comprises $KNO_3$; $TiNO_3$; and $Cu(NO_3)_2$ $2.5.H_2O$.

27. The method of claim 7, wherein said inorganic nitrate salt comprises $KNO_3$; $TiNO_3$; and $Zn(NO_3)_2$ $6.H_2O$.

28. The method of claim 7, wherein said inorganic nitrate salt comprises $KNO_3$; $TiNO_3$; and $Pb(NO_3)_2$.

29. The method of claim 7, wherein said inorganic nitrate salt comprises $KNO_3$; $Cu(NO_3)_2$ $2.5.H_2O$; and $Fe(NO_3)_3$ $9.H_2O$.

30. The method of claim 7, wherein said inorganic nitrate salt comprises $KNO_3$; $Cu(NO_3)_2$ $2.5.H_2O$; $Hg(NO_3)_2.H_2O$; and $Zn(NO_3)_2$ $6.H_2O$.

31. The method of claim 7, wherein said inorganic nitrate salt comprises $KNO_3$; $LiNO_3$; $Cu(NO_3)_2 2.5.H_2O$; $Hg(NO_3)_2.H_2O$; and $Fe(NO_3)_3$ $9.H_2O$.

32. The method of claim 7, wherein said inorganic nitrate salt comprises $KNO_3$; $LiNO_3$; $AgNO_3$; $Cu(NO_3)_2$ $2.5.H_2O$; $Hg(NO_3)_2.H_2O$; and $Fe(NO_3)_3$ $9.H_2O$.

33. The method of claim 7, wherein said inorganic nitrate salt comprises $KNO_3$; $LiNO_3$; $Zn(NO_3)_2$ $6.H_2O$; $Cu(NO_3)_2$ $2.5\ H_2O$; $Hg(NO_3)_2.H_2O$; and $Fe(NO_3)_3$ $9.H_2O$.

34. The method of claim 7, wherein said inorganic nitrate salt comprises $KNO_3$; $Zn(NO_3)_2$ $6.H_2O$; $Cu(NO_3)_2$ $2.5.H_2O$; $Hg(NO_2)_2.H_2O$; and $Fe(NO_3)_3$ $9.H_2O$.

35. The method of claim 1, further comprising the step of purifying the 9-nitrocamptothecin by column chromatography.

36. The method of claim 35, wherein said column chromatography is conducted with an element comprising tetrahydrofuran and methylene chloride.

37. The method of claim 1, further comprising purifying the 9-nitrocamptothecin by reprecipitation from ethanol.

38. The method of claim 1, wherein said inorganic nitrate salt comprises thallium nitrate.

39. The method of claim 1, wherein said inorganic nitrate salt comprises potassium nitrate and thallium nitrate.

40. The method of claim 1, wherein said inorganic nitrate salt is thallium nitrate and said acid is sulfuric acid.

*41. 9-nitrocamptothecin in crystalline form wherein the crystalline form has a melting point of at least 268° C.*

*42. A method of crystallizing 9-nitrocamptothecin comprising:*

*performing a crystallization process on 9-nitrocamptothecin wherein ethanol is employed as the primary solvent to form crystalline 9-nitrocaptothecin having a yellow color and a melting point of at least 268° C.*

* * * * *